United States Patent [19]

Cretois et al.

[11] Patent Number: 6,060,044
[45] Date of Patent: *May 9, 2000

[54] COSMETIC COMPOSITION BASED ON GUAR GUM AND SILICONES

[75] Inventors: Isabelle Cretois, Clichy; Henri Samain, Bievres, both of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/940,195

[22] Filed: Sep. 29, 1997

Related U.S. Application Data

[63] Continuation of application No. 08/592,483, Jan. 26, 1996, abandoned.

[30] Foreign Application Priority Data

Jan. 27, 1995 [FR] France ................................ 95 00983

[51] Int. Cl.⁷ ..................................................... A61K 7/075
[52] U.S. Cl. ........................................................ 424/70.12
[58] Field of Search ........................................... 424/70.12

[56] References Cited

U.S. PATENT DOCUMENTS

| | | | |
|---|---|---|---|
| 4,839,167 | 6/1989 | Yamamoto et al. | 424/71 |
| 5,188,756 | 2/1993 | Baker et al. | 252/174.15 |
| 5,217,652 | 6/1993 | Iovanni | 252/347 |
| 5,306,489 | 4/1994 | Goldberg et al. | 424/71 |
| 5,344,643 | 9/1994 | Thiel et al. | 424/70 |
| 5,439,682 | 8/1995 | Wivell et al. | 724/401 |
| 5,470,884 | 11/1995 | Corless et al. | 514/714 |

FOREIGN PATENT DOCUMENTS

| | | |
|---|---|---|
| A-562638 | 9/1993 | European Pat. Off. . |
| A-633018 | 1/1995 | European Pat. Off. . |
| A-2707163 | 1/1995 | France . |
| A-2079954 | 3/1995 | France . |
| 63-183520 | 7/1988 | Japan . |
| 63-188617 | 8/1988 | Japan . |
| 2-124811 | 5/1990 | Japan . |
| 4-112808 | 4/1992 | Japan . |
| 6-128127 | 5/1994 | Japan . |
| 6-312915 | 11/1994 | Japan . |
| 6-321739 | 11/1994 | Japan . |
| A-2173515 | 10/1986 | United Kingdom . |

OTHER PUBLICATIONS

Derwent Abstract of FR–A–2079954.
Derwent Abstract of EP–A–633018.
Derwent Abstract of FR–A–2707163.
Derwent abstract of JP 6–312915.
Derwent abstract of JP 6–128127.
Derwent abstract of JP 63–188617.
Derwent abstract of JP 63–183520.
Derwent abstract of JP 2–124811.
Derwent abstract of JP 4–112808.
Derwent abstract of JP 6–321739.

*Primary Examiner*—Margaret G. Moore
*Attorney, Agent, or Firm*—Finnegan, Henderson, Farabow, Garrett & Dunner, L.L.P.

[57] ABSTRACT

A non-washing cosmetic composition comprising, in a cosmetically acceptable medium, at least one guar gum and at least one oxyalkylenated silicone in a guar gum/silicone weight ratio of less than or equal to 5:1, and a process for the treatment of the skin or keratinous fibres comprising the step of applying a non-washing cosmetic composition as defined above to the skin or to the keratinous fibres and optionally rinsing the skin or keratinous fibres with water.

27 Claims, No Drawings

COSMETIC COMPOSITION BASED ON GUAR GUM AND SILICONES

This application is a continuation of application Ser. No. 08/592,483, filed Jan. 26, 1996 now abandoned.

The present invention relates to cosmetic compositions containing, in a cosmetically acceptable medium, at least one guar gum and at least one oxyalkylenated silicone in a guar gum/silicone weight ratio of less than or equal to 5.

Another subject of the invention is a process for the non-washing cosmetic treatment of keratinous material, such as the hair or the eyelashes, characterized in that it includes applying a cosmetic composition as defined above to the keratinous material, optionally followed by rinsing with water. As is readily understood by those skilled in the art, non-washing compositions do not have detergent properties, i.e., these compositions contain less than 3% detergent surfactants.

Formulations which make it possible to fix and to condition the hair are already known in the state of the art. Compositions in gel form which are generally based on crosslinked acrylic polymers have already been used with this aim. However, these compositions have the drawback of leaving an undesirable deposit on the hair, which is detrimental to the cosmetic properties thereof: thus, at the end of the operation, the hair lacks shine, is coarse or is sticky.

The use of silicone-containing derivatives in combination with polymer resins is known in the preparation of cosmetic compositions for holding the hairstyle. It has been observed that these silicone-containing derivatives clearly improve the properties of disentangling, softness and shine of hair treated using these compositions, although these properties are generally inferior to the properties of the silicone derivative used alone.

Unfortunately, however, these silicone-containing derivatives are not generally favourable towards the fixing power of these compositions, which fixing power is provided by the polymer resin.

In particular, oxyalkylenated silicones are generally known for not imparting hold to the head of hair. Guar gums have been described in the art as being thickeners. In particular, they have been used to thicken conditioning compositions containing volatile silicones in application EP-A-0,035,901.

The inventors have discovered that the combination of guar gums with oxyalkylenated silicones in a specific ratio led, surprisingly and unexpectedly, to particularly advantageous properties, in particular to an improvement in the hold of the hairstyle over time. The head of hair has more volume, and the hair is shiny and has a natural feel. This discovery forms the basis of the present invention.

The subject of the present invention is thus novel non-washing cosmetic compositions for keratinous material such as the hair, the skin or the eyelashes, characterized in that they contain, in a cosmetically acceptable non-detergent medium, at least one guar gum and at least one oxyalkylenated silicone in a guar gum/silicone weight ratio of less than or equal to 5:1.

Other characteristics, aspects, subjects and advantages of the invention will emerge even more clearly on reading the description and the examples which follow.

The guar gums which may be used according to the invention are preferably nonionic or cationic. According to the invention, unmodified or chemically modified nonionic guar gums are preferably used. Unmodified nonionic guar gums are, for example, the products sold under the name VIDOGUM GH 175 by the company Unipectine and under the name JAGUAR C by the company Meyhall. Modified nonionic guar gums which may be used according to the invention are preferably modified with $C_1$–$C_6$ hydroxyalkyl groups. Among the hydroxyalkyl groups which may be mentioned by way of example are hydroxymethyl, hydroxyethyl, hydroxypropyl and hydroxybutyl groups.

These guar gums are well known in the state of the art and may be prepared, for example, by reacting corresponding alkene oxides, for example such as propylene oxides, with guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2. Such nonionic guar gums optionally modified with hydroxyalkyl groups are sold, for example, under the trade names JAGUAR HP8, JAGUAR HP60 and JAGUAR HP120, JAGUAR DC 293 and JAGUAR HP 105 by the company Meyhall, or under the name GALACTASOL 4H4FD2 by the company Aqualon.

The cationic guar gums which may more particularly be used according to the invention are guar gums containing trialkylammonium cationic groups. Preferably, 2 to 30%, and even more preferably 5 to 20%, in numerical terms, of the hydroxyl functions of these guar gums bear trialkylammonium cationic groups.

Among these trialkylammonium groups, there may most particularly be mentioned trimethylammonium and triethylammonium groups. Even more preferably, these groups represent from 5 to 20% by weight relative to the total weight of the modified guar gum.

According to the invention, a guar gum modified with 2,3-epoxypropyltrimethylammonium chloride is preferably used.

These guar gums modified with cationic groups are products which are already known per se and are described, for example, in U.S. Pat. Nos. 3,589,578 and 4,031,307, the disclosures of which are expressly incorporated by reference herein. Such products are, moreover, sold in particular under the trade names JAGUAR C13 S, JAGUAR C 15 and JAGUAR C 17 by the company Meyhall.

A nonionic guar gum is preferably used and, among these nonionic guar gums, guar gums modified with hydroxyalkyl groups are more particularly used.

The silicones modified with oxyalkylene groups, including monovalent oxyalkylenated groups, are preferably chosen, for example, from the compounds of general formulae (I), (II), (III) and (IV):

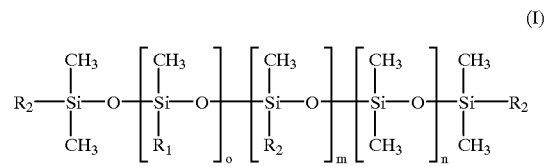

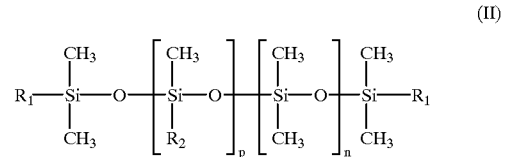

-continued $$R_2-\underset{\underset{CH_3}{|}}{\overset{\overset{CH_3}{|}}{Si}}-O-\left[\underset{\underset{R_1}{|}}{\overset{\overset{CH_3}{|}}{Si}}-O\right]_o\left[\underset{\underset{CH_3}{|}}{\overset{\overset{CH_3}{|}}{Si}}-O\right]_n\underset{\underset{CH_3}{|}}{\overset{\overset{CH_3}{|}}{Si}}-R_2 \qquad (III)$$

$$R_3-Si\left[-O-\underset{\underset{CH_3}{|}}{\overset{\overset{CH_3}{|}}{Si}}\right]_x-(OC_2H_4)_a(OC_3H_6)_bOR_4\right]_3 \qquad (IV)$$

in which formulae:

$R_1$ represents a phenyl or $C_1$–$C_{30}$ alkyl radical, $R_2$ represents $(CH_2)_c(-C_2H_4O)_a(-C_3H_6O)_b-R_5$, $R_3$ and $R_4$, which may be identical or different, denote a $C_1$–$C_{12}$ alkyl radical, $R_5$ is chosen from a hydrogen atom, an alkyl radical of 1 to 12 carbon atoms, an alkoxy radical of 1 to 6 carbon atoms, a hydroxyl radical, —$SO_3M$, —$OCOR_6$, $C_1$–$C_6$ aminoalkoxy optionally substituted on the amine, $C_1$–$C_6$ aminoacyl optionally substituted on the amine, —$NHCH_2CH_2COOM$, $N(CH_2CH_2COOM)_2$, aminoalkyl, preferably containing from one to six carbon atoms, optionally substituted on the amine and on the alkyl chain, $C_1$–$C_{30}$ carboxyacyl, a phosphono group optionally substituted with one or two substituted aminoalkyl radicals, —$CO(CH_2)_dCOOM$, —$OCOCHR_7(CH_2)_dCOOM$, —$NHCO(CH_2)_dOH$ and $NH_3Y$, M denotes a hydrogen atom, Na, K, Li, $NH_4$ or an organic amine, $R_6$ denotes a $C_1$–$C_{30}$ alkyl radical, $R_7$ denotes hydrogen or $SO_3M$, d ranges from 1 to 10, m ranges from 0 to 20, n ranges from 1 to 100, o ranges from 0 to 20, p ranges from 1 to 20, a ranges from 0 to 50, b ranges from 0 to 50, a+b is greater than or equal to 1, c ranges from 0 to 4, x ranges from 1 to 100, Y represents a monovalent inorganic or monovalent organic anion.

Silicones corresponding to the general formula (I) or (II) are preferably used, and in particular those in which R5 denotes a hydrogen atom.

Preferably, c is equal to 2 or 3.

Such silicones are sold, for example, by the company Goldschmidt under the trade names ABIL WE 09, ABIL EM 90, ABIL B8852, ABIL B8851, ABIL B 8843 and ABIL B8842, by the company Dow Corning under the names FLUID DC 190, DOW CORNING 193, DC 3225 C, Q2-5220, Q2-5354 and Q2-5200, by the company Rhône-Poulenc under the names SILBIONE OIL 70646 and RHODORSIL OIL 10634, by the company General Electric under the names SF1066 and SF1188, by the company SWS Silicones under the name SILICONE COPOLYMER F 754, by the company Amerchol under the name SILSOFT BEAUTY AID SL, by the company Shin-Etsu under the name KF 351, by the company Wacker under the name BELSIL DMC 6038, by the company Siltech under the names SILWAX WD-C, SILWAX WD-B, SILWAX WD-IS, SILWAX WS-L, SILWAX DCA 100 and SILTECH AMINE 65, and by the company Fanning Corporation under the names FANCORSIL SLA and FANCORSIL LIM1.

The concentration of guar gum may range from 0.01% to 5% by weight approximately relative to the total weight of the composition, and preferably from 0.1 to 2.5% approximately. The concentration of oxyalkylenated silicone may range from 0.01 to 5% by weight approximately relative to the total weight of the composition, and preferably from 0.1 to 2.5% approximately. The guar gum/oxyalkylenated silicone weight ratio is preferably from 0.1:1 to 4:1.

The cosmetically acceptable medium preferably comprises water or a mixture of water and cosmetically acceptable solvents such as monoalcohols, polyalcohols, glycol ethers or fatty acid esters, which may be used alone or as a mixture.

There may more particularly be mentioned lower alcohols such as ethanol and isopropanol, polyalcohols such as diethylene glycol, glycol ethers, glycol alkyl ethers or diethylene glycol.

The pH of the compositions according to the invention generally ranges from 2 to 9, and in particular from 3 to 8. The pH may be adjusted to the chosen value using basifying or acidifying agents usually used in cosmetics for this type of application.

The compositions according to the invention may also contain thickeners, surfactants, preserving agents, sequestering agents, softeners, fragrances, dyes, viscosity modifiers, foam modifiers, foaming agents, foam stabilizers, pearling agents, moisturizing agents, antidandruff agents, antiseborrhoeic agents, sunscreens, proteins, vitamins, plasticizers, hydroxy acids, electrolytes, propellants and fragrances.

The compositions according to the invention may also contain conditioners. In this case, the conditioners may be chosen from natural or synthetic oils and waxes, fatty alcohols, polyhydric alcohol esters, glycerides, silicone oils, gums and resins, or mixtures of these various compounds.

Another subject of the invention is a process for the non-washing cosmetic treatment of keratinous material, such as the skin, the hair or the eyelashes, characterized in that the invention comprises applying a cosmetic composition as defined above to the keratinous material, and optionally, in rinsing, after an optional period of exposure of the keratinous material to the composition. Thus, this process according to the invention makes it possible to maintain the hairstyle or the eyelashes, and to treat and care for the skin, the hair or any other keratinous material.

The cosmetic compositions according to the invention may be in the form of a gel, a milk, a cream, a cream-gel, a spray, a more or less thickened lotion or a mousse, and may be used, for example, for the skin, the hair, the eyelashes or the eyebrows.

For the hair, the cosmetic compositions according to the invention can be particularly useful as rinsing or leave-in compositions, to be applied before or after a shampooing, dyeing, bleaching, permanent-waving or hair-straightening operation. The compositions may also be hair setting lotions, blow-drying lotions, fixing compositions and styling compositions.

The lotions may be packaged in various forms, in particular in vaporizers, pump-dispenser bottles or aerosol containers in order to provide application of the composition in vaporized form or in the form of a mousse. Such packaging forms are indicated, for example, when it is desired to obtain a spray, a lacquer or a foam for fixing or treating the hair.

When the composition according to the invention is packaged in the form of an aerosol for the purpose of obtaining a lacquer or an aerosol mousse, it comprises at least one propellant which may be chosen from volatile hydrocarbons such as n-butane, propane, isobutane and pentane, chlorinated and/or fluorinated hydrocarbons, and mixtures thereof. It is also possible to use compressed air, nitrogen, dimethyl ether, nitrous oxide or carbon dioxide as propellant.

In all of the following text or in the preceding text, the percentages are expressed by weight.

The invention will now be illustrated more fully by means of the examples which follow, which should not be considered as limiting the invention to the embodiments described.

In the examples, AM means active material.

EXAMPLE 1

A gel (1), in accordance with the invention, having the following composition was prepared:

| | |
|---|---|
| Nonionic guar gum modified with hydroxypropyl groups, sold under the trade name JAGUAR HP60 by the company Meyhall | 1.7 g |
| Dimethicone copolyol (INCI) (Q2-5220 from Dow Corning) | 2 g |
| Water | qs 100 g |

A gel (2), according to the invention, of the following composition was prepared:

| | |
|---|---|
| Cationic guar gum sold under the trade name JAGUAR C13S by the company Meyhall | 1.7 g |
| Dimethicone copolyol (INCI) (Q2-5220 from Dow Corning) | 2 g |
| Water | qs 100 g |

A comparative gel (3) of the following composition was prepared:

| | |
|---|---|
| Crosslinked acrylic acid polymer sold under the trade name CARBOPOL 940 by the company Goodrich | 1.7 g |
| Dimethicone copolyol (INCI) (Q2-5220 from Dow Corning) | 2 g |
| Monoethanolamine | qs pH 7 |
| Demineralized water | qs 100 g |

A comparative gel (4) of the following composition was prepared:

| | |
|---|---|
| Vinyl acetate/vinylpyrrolidone copolymer sold under the trade name LUVISKOL VA 64 by the company BASF | 1.7 g |
| Dimethicone copolyol (INCI) (Q2-5220 from Dow Corning) | 2 g |
| Water | qs 100 g |

0.5 g of gel per g of hair was applied to locks of washed and drained hair. The hair was then blow-dried.

A panel of 8 judges was then asked to evaluate the holding of the style (firmness of the fibre) and the feel of the hair.

Assessment:

Holding of the style: 0 (no holding) to 5 (very strong fixing)

Feel: 0 (very poor) to 5 (excellent)

After 5 hours at ambient temperature and humidity, the same judges evaluated the hold of the hairstyle.

Assessment:

Hold: 0 (no hold) to 5 (perfect hold)

The results (average of the ratings) are collated in the table below:

| | Holding | Feel | Hold |
|---|---|---|---|
| Gel (1) invention | 4.25 | 4.75 | 4 |
| Gel (2) invention | 5 | 4.5 | 4.25 |
| Gel (3) | 1.75 | 3.75 | 1.5 |
| Gel (4) | 4.25 | 1.25 | 3 |

Only gels 1 and 2 according to the invention have very good holding, feel and hold properties.

A comparative gel (5) of the following composition was also prepared:

| | |
|---|---|
| Nonionic guar gum modified with hydroxypropyl groups, sold under the trade name JAGUAR HP60 by the company Meyhall | 1.7 g |
| Cyclic volatile silicone (DC 245 fluid from Dow Corning) | 2 g |
| Water | qs 100 g |

A comparative gel (6) of the following composition was also prepared:

| | |
|---|---|
| Nonionic guar gum modified with hydroxypropyl groups, sold under the trade name JAGUAR HP60 by the company Meyhall | 1.7 g |
| Amodimethicone (DC 929 cationic emulsion from Dow Corning) at a concentration of 35% AM | 2 gAM |
| Water | qs 100 g |

0.5g of gel per g of hair was applied to locks of washed and drained hair. The hair was then blow-dried.

A panel of 8 judges was then asked to evaluate the holding of the style, the feel and the hold of the hairstyle.

The results (average of the ratings) are collated in the table below:

| | Holding | Feel | Hold |
|---|---|---|---|
| Gel (1) invention | 4.25 | 4.75 | 4 |
| Gel (5) | 3.25 | 3 | 3.25 |
| Gel (6) | 3 | 3.5 | 2.75 |

Gel (1) according to the invention has better holding, feel and hold properties than the compositions containing silicones already used in the compositions of the prior art.

EXAMPLE 2

A gel of the following composition was prepared:

| | |
|---|---|
| Nonionic guar gum modified with hydroxypropyl groups, sold under the trade name JAGUAR HP60 by the company Meyhall | 1.2 g |
| Dimethicone copolyol (INCI) (SILBIONE oil 70646 from Rhone-Poulenc) | 0.5 g |
| Carbomer (INCI) (SYNTHALEN K from 3V) | 0.25 g |
| Triethanolamine | qs pH 7.2 |
| Ethanol | 15 g |
| Water | qs 100 g |

This gel is applied to wet hair (about 5 g per head), and the hair is then blow-dried.

The hair is well-behaved, shiny, and has a natural feel.

The hairstyle hold obtained is very good.

This gel may also be applied to dry hair. While putting on the gel, the hair is placed in shape by hand.

The hairstyle hold obtained is very good.

EXAMPLE 3

A gel of the following composition was prepared:

| | |
|---|---|
| Cationic guar gum sold under the trade name JAGUAR C13S by the company Meyhall | 1.5 g |
| Dimethicone copolyol (INCI) (Q2-5220 from Dow Corning) | 2 g |
| Polyvinylpyrrolidone (PVP K30 from ISP) | 0.3 g |
| Ethanol | 12 g |
| Water | qs 100 g |

This gel is applied to washed, wet hair (about 10 g per head), the roots are bleached and the hair is then dried under a hood for about 30 minutes. The hair is then brushed through.

The hairstyle is bouffant, and the hair has a natural feel.

The hairstyle hold obtained is very good.

EXAMPLE 4

A styling mousse of the following composition was prepared:

| | |
|---|---|
| Nonionic guar gum modified with hydroxypropyl groups, sold under the trade name JAGUAR HP60 by the company Meyhall | 0.5 g |
| Dimethicone copolyol (INCI) sold by the company Dow Corning under the name Q2-5220 | 1 g |
| Polyquaternium-4 (INCI) sold under the name CELQUAT L200 by the company National Starch | 0.2 g |
| Polyquaternium-11 (INCI) sold at a concentration of 50% AM in ethanol, under the name GAFQUAT 734 by the company ISP | 0.3 gAM |
| Ethyl alcohol | 10 g |
| Fragrance, preserving agent | qs |
| Demineralized water | qs 100 g |

Packaging as an aerosol:

90 g of the above composition are packaged in an aerosol container in the presence of 10 g of a ternary mixture of n-butane, isobutane and propane (23/55/22), sold under the name AEROGAZ 3.2 N by the company Elf Aquitaine This mousse has a very pleasant creamy texture.

This mousse is applied to wet hair; it spreads easily over the entire head of hair and facilitates disentangling of the hair.

The hair is then blow-dried; the hairstyle obtained is bouffant; the hair is shiny, without residues and has a natural feel.

The hairstyle has good hold over time.

What is claimed is:

1. A non-washing cosmetic composition for application to the hair, comprising, in a cosmetically acceptable medium, at least one guar gum and at least one silicone modified with at least one oxyalkylenated group in a guar gum/silicone weight ratio of less than or equal to 5:1, said guar gum/silicone weight ratio being an amount intended to provide styling properties to hair, wherein said at least one silicone modified with at least one oxyalkylene group is chosen from the compounds of formulae (I), (II), (III) and (IV):

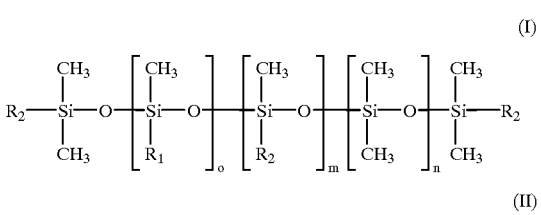

(I)

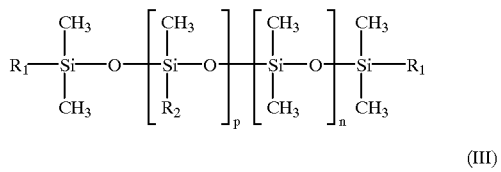

(II)

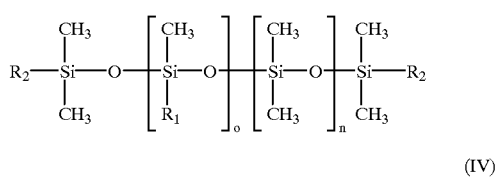

(III)

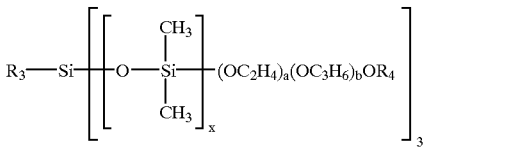

(IV)

in which formulae:

each $R_1$ can be the same or different and is a phenyl or $C_1$–$C_{30}$ alkyl radical, each $R_2$ can be the same or different and is $(CH_2)_c(-C_2H_4O)_a(-C_3H_6O)_b-R_5$, $R_3$ is a $C_1$–$C_{12}$ alkyl radical, each $R_4$ can be the same or different and is a $C_1$–$C_{12}$ alkyl radical, each $R_5$ can be the same or different and is chosen from a hydrogen atom, a $C_1$–$C_{12}$ alkyl radical, a $C_1$–$C_6$ alkoxy radical, a hydroxyl radical, —SO$_3$M, —OCOR$_6$, $C_1$–$C_6$ aminoalkoxy radical, a $C_1$–$C_6$ aminoacyl radical, —NHCH$_2$CH$_2$COOM, N(CH$_3$CH$_3$COOM)$_2$, an aminoalkyl radical, a $C_1$–$C_{30}$ carboxyacyl radical, a phosphono group containing one or two aminoalkyl radicals, —CO(CH$_2$)$_d$COOM, —OCOCHR$_7$(CH$_2$)$_d$COOM, —NHCO(CH$_2$)$_d$OH and NH$_3$Y, M is a hydrogen atom, Na, K, Li, $NH_4$ or an organic amine, $R_6$ is a $C_1$–$C_{30}$ alkyl radical, $R_7$ is hydrogen or $SO_3M$, d ranges from 1 to 10, m ranges from 0 to 20, n ranges from 1 to 100, o ranges from 0 to 20, p ranges from 1 to 20, a ranges from 0 to 50, b ranges from 0 to 50, a+b is greater than or equal to 1, c ranges from 0 to 4, x ranges from 1 to 100, and Y is a monovalent inorganic or organic anion.

2. The composition as claimed in claim 1, wherein said at least one guar gum is selected from nonionic and cationic guar gums.

3. The composition as claimed in claim 2, wherein said at least one guar gum is a nonionic guar gum.

4. The composition as claimed in claim 3, wherein said nonionic guar gum is modified with $C_1$–$C_6$ hydroxyalkyl groups.

5. The composition as claimed in claim 4, wherein said hydroxyalkyl groups are selected from hydroxymethyl, hydroxyethyl, hydroxypropyl and hydroxybutyl groups.

6. The composition as claimed in claim 3, wherein said at least one nonionic guar gum has a degree of hydroxyalkylation ranging from 0.4 to 1.2.

7. The composition as claimed in claim 2, wherein said at least one guar gum is a cationic guar gum containing trialkylammonium groups.

8. The composition as claimed in claim 7, wherein said trialkylammonium groups are selected from trimethylammonium and triethylammonium groups.

9. The composition as claimed in claim 7, wherein the trialkylammonium groups represent less than 30% by weight relative to the total weight of the guar gum.

10. The composition as claimed in claim 9, wherein the trialkylammonium groups represent from 5 to 20% by weight relative to the total weight of the guar gum.

11. The composition as claimed in claim 7, wherein said at least one guar gum is modified with 2,3-epoxypropyltrimethylammonium chloride.

12. The composition as claimed in claim 1, wherein said at least one silicone modified with at least one oxyalkylene group corresponds to the general formula (I) or (II).

13. The composition as claimed in claim 12, wherein $R_5$ denotes a hydrogen atom.

14. The composition as claimed in claim 1, wherein said at least one guar gum is present in an amount of from 0.01% to 5% by weight approximately relative to the total weight of the composition.

15. The composition as claimed in claim 1, wherein said at least one silicone modified with at least one oxyalkylenated group is present in an amount of from 0.01% to 5% by weight approximately relative to the total weight of the composition.

16. The composition as claimed in claim 1, wherein the cosmetically acceptable medium comprises water or a mixture of water and at least one cosmetically acceptable solvent, wherein said solvent is a monoalcohol, polyalcohol, glycol ether or fatty acid ester.

17. The composition as claimed in claim 1, further comprising surfactants, thickeners, preserving agents, sequestering agents, softeners, fragrances, dyes, viscosity modifiers, foam modifiers, foaming agents, foam stabilizers, pearling agents, moisturizing agents, antidandruff agents, antiseborrhoeic agents, sunscreens, proteins, vitamins, plasticizers, hydroxy acids, electrolytes, propellants, fragrances or conditioners.

18. The composition as claimed in claim 1, wherein the composition is in the form of a gel, a milk, a cream, a cream-gel, a spray, a lotion or a mousse.

19. A process for the non-washing cosmetic treatment of keratinous material, comprising applying a composition as claimed in claim 1 to said keratinous material.

20. The process as claimed in claim 19, further comprising the step of exposing the keratinous material to the composition.

21. The process as claimed in claim 19, further comprising the step of rinsing said keratinous material after said step of applying.

22. A composition as claimed in claim 1, wherein said guar gum/silicone weight ratio ranges from 0.1:1 to 4:1.

23. The composition as claimed in claim 8, wherein the trialkylammonium groups represent less than 30% by weight relative to the total weight of the modified guar gum.

24. A process for the non-washing cosmetic treatment of hair said process comprising applying a nonwashing composition comprising, in a cosmetically acceptable medium, at least one guar gum and at least one silicone modified with at least one oxyalkylenated group in a guar gum/silicone weight ratio of less than or equal to 5:1 to said hair.

25. A process for the non-washing cosmetic treatment of hair said process comprising applying a nonwashing composition comprising, in a cosmetically acceptable medium, at least one guar gum and at least one silicone modified with at least one oxyalkylenated group in a guar gum/silicone weight ratio of less than or equal to 5:1 to said hair, wherein said at least one silicone modified with at least one oxyalkylene group is chosen from the compounds of formulae (I), (II), (III) and (IV):

$$R_2\text{—}\underset{\underset{CH_3}{|}}{\overset{\overset{CH_3}{|}}{Si}}\text{—}O\text{—}\left[\underset{\underset{R_1}{|}}{\overset{\overset{CH_3}{|}}{Si}}\text{—}O\right]_o\text{—}\left[\underset{\underset{R_2}{|}}{\overset{\overset{CH_3}{|}}{Si}}\text{—}O\right]_m\text{—}\left[\underset{\underset{CH_3}{|}}{\overset{\overset{CH_3}{|}}{Si}}\text{—}O\right]_n\text{—}\underset{\underset{CH_3}{|}}{\overset{\overset{CH_3}{|}}{Si}}\text{—}R_2 \quad (I)$$

$$R_1\text{—}\underset{\underset{CH_3}{|}}{\overset{\overset{CH_3}{|}}{Si}}\text{—}O\text{—}\left[\underset{\underset{R_2}{|}}{\overset{\overset{CH_3}{|}}{Si}}\text{—}O\right]_p\text{—}\left[\underset{\underset{CH_3}{|}}{\overset{\overset{CH_3}{|}}{Si}}\text{—}O\right]_n\text{—}\underset{\underset{CH_3}{|}}{\overset{\overset{CH_3}{|}}{Si}}\text{—}R_1 \quad (II)$$

(III)

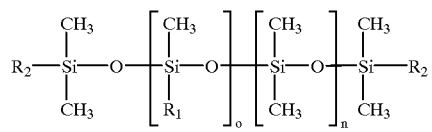

(IV)

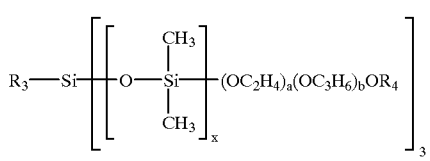

in which formulae:
- each $R_1$ can be the same or different and is a phenyl of $C_1$–$C_{30}$ alkyl radical,
- each $R_2$ can be the same or different and is $(CH_2)_c(\text{—}C_3H_4O)_a(\text{—}C_3H_6O)_b\text{—}R_5$,
- $R_3$ is a $C_1$–$C_{12}$ alkyl radical,
- each $R_1$ can be the same or different and is a $C_1$–$C_{12}$ alkyl radical,
- each $R_5$ can be the same or different and is chosen from a hydrogen atom, a $C_1$–$C_{12}$ alkyl radical, a $C_1$–$C_6$ alkoxy radical, a hydroxyl radical, —$SO_3M$, —$OCOR_6$ a $C_1$–$C_6$ aminoalkoxy radical, a $C_1$–$C_6$ aminoacyl radical, —$NHCH_2CH_2COOM$, $N(CH_3CH_3COOM)_2$, an aminoalkyl radical, a $C_1$–$C_{30}$ carboxyacyl radical, a phosphono group containing one or two aminoalkyl radicals, —$CO(CH_2)_dCOOM$, —$OCOCHR_7(CH_2)_dCOOM$, —$NHCO(CH_2)_dOH$ and $NH_3Y$,
- M is a hydrogen atom, Na, K, Li, $NH_4$ or an organic amine.
- $R_6$ is a $C_1$–$C_{30}$ alkyl radical,
- $R_7$ is hydrogen or $SO_3M$,
- d ranges from 1 to 10,
- m ranges from 0 to 20,
- n ranges from 1 to 100,
- o ranges from 0 to 20,
- p ranges from 1 to 20,
- a ranges from 0 to 50,
- b ranges from 0 to 50,
- a+b is greater than or equal to 1,
- c ranges from 0 to 4,
- x ranges from 1 to 100, and
- Y is a monovalent inorganic or organic anion.

26. The process for the non-washing cosmetic treatment of hair according to claim 25, wherein said hair is eyelashes.

27. The process for the non-washing cosmetic treatment of hair according to claim 25, wherein said hair is eyebrows.

* * * * *